US00PP37777P3

(12) United States Plant Patent
Schoone

(10) Patent No.: US PP37,777 P3
(45) Date of Patent: Oct. 13, 2026

(54) ***PHALAENOPSIS* PLANT NAMED 'Helios'**

(50) Latin Name: ***Phalaenopsis* hybrida**
Varietal Denomination: Helios

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/631,767

(22) Filed: Mar. 27, 2026

(65) Prior Publication Data

US 2026/0305507 P1 Oct. 1, 2026

Related U.S. Application Data

(60) Provisional application No. 63/781,328, filed on Mar. 31, 2025.

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Helios', characterized by its upright plant habit; moderately vigorous to vigorous growth habit; semi-erect to horizontal leaves; freely flowering habit with typically two inflorescences developing per plant, each inflorescence with numerous flowers; flowers with light yellow green-colored petals and sepals; and good postproduction longevity.

2 Drawing Sheets

Figure 1:
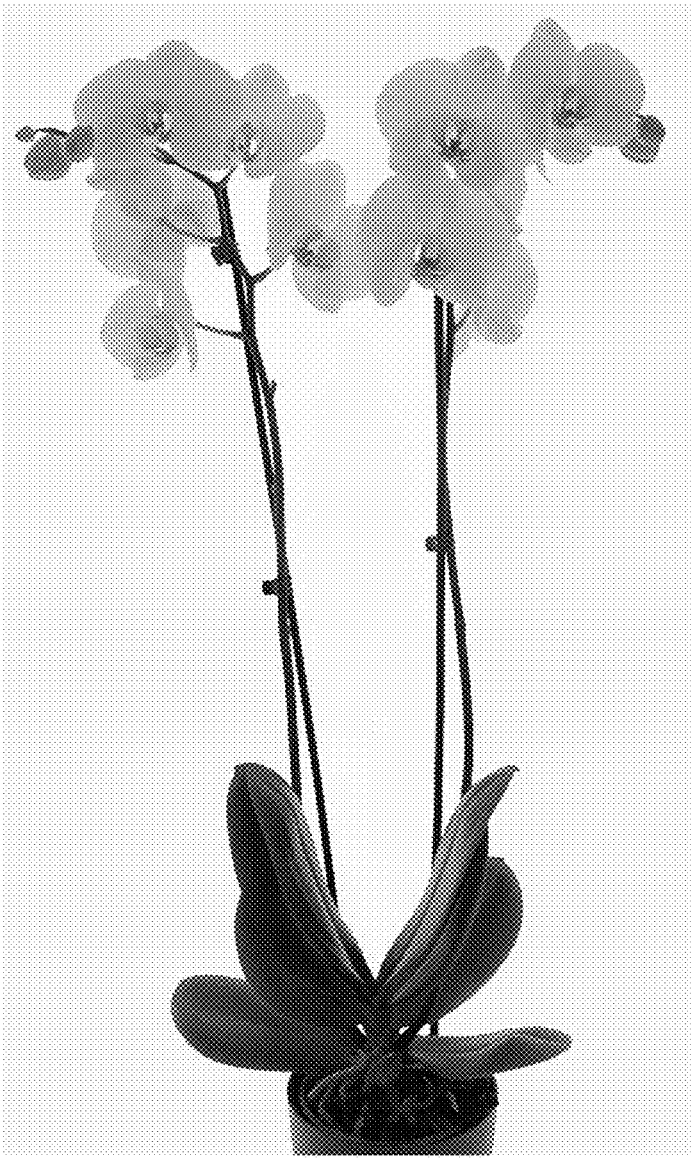

Botanical designation: *Phalaenopsis* hybrida.

Cultivar denomination: 'HELIOS'.

A European Community Plant Breeder's Rights application for the instant plant was filed by the Applicant/Assignee, Floricultura B.V. of Heemskerk, The Netherlands on Jun. 23, 2025, application number 2025/1317. Foreign priority is not claimed to this application.

BACKGROUND OF THE INVENTION

The present invention relates to a new and distinct cultivar of Phalaenopsis plant, botanically known as *Phalaenopsis* hybrida, and hereinafter referred to by the name 'Helios'.

The new *Phalaenopsis* plant is a product of a planned breeding program conducted by the Inventor in Heemskerk and Assendelft, The Netherlands. The objective of the breeding program is to develop new fast-growing and freely flowering *Phalaenopsis* plants with good leaf shape and strength and flowers with unique and attractive patterns and coloration.

The new *Phalaenopsis* plant originated from a cross-pollination on May 18, 2015 in Heemskerk, The Netherlands of a proprietary selection of *Phalaenopsis* hybrida identified as code name C.L., not patented, as the female, or seed, parent with *Phalaenopsis* hybrida 'Emeraude', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in July 2021.

Asexual reproduction of the new *Phalaenopsis* plant by in vitro meristem propagation in a controlled environment in Assendelft, The Netherlands since August 2022 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Helios'. These characteristics in combination distinguish 'Helios' as a new and distinct *Phalaenopsis* plant:

1. Upright plant habit.
2. Moderately vigorous to vigorous growth habit.
3. Semi-erect to horizontal leaves.
4. Freely flowering habit with typically two inflorescences developing per plant, each inflorescence with numerous flowers.
5. Flowers with light yellow green-colored petals and sepals.
6. Good postproduction longevity.

Plants of the new *Phalaenopsis* can be compared to plants of the female parent selection. Plants of the new *Phalaenopsis* differ primarily from plants of the female parent selection in the following characteristics:

1. The labella central lobes of plants of the new *Phalaenopsis* are light yellow green in color with dark pink-colored bases whereas the labella central lobes of plants of the female parent selection are yellow and white in color.

2. The flower column of plants of the new *Phalaenopsis* are light yellow green in color whereas the flower column of plants of the female parent selection are white in color.

Plants of the new *Phalaenopsis* can be compared to plants of the male parent, 'Emeraude'. Plants of the new *Phalaenopsis* differ primarily from plants of 'Emeraude' in the following characteristics:

1. Petals of plants of the new *Phalaenopsis* are not as separate as petals of plants of 'Emeraude'.
2. The labella central lobes of plants of the new *Phalaenopsis* are light yellow green in color with dark pink-colored bases whereas the labella central lobes of plants of 'Emeraude' are dark yellow in color with creamy white apices.

Plants of the new *Phalaenopsis* can be compared to plants of x *Phalaenopsis* hybrida 'Mint', disclosed in U.S. Plant Pat. No. 36,267. In side-by-side comparisons, plants of the new *Phalaenopsis* differ primarily from plants of 'Mint' in the following characteristics:

1. Petals of plants of the new *Phalaenopsis* are not as separate as petals of plants of 'Mint'.
2. Dots on peduncles of plants of the new *Phalaenopsis* are darker in color than dots on peduncles of plants of plants of 'Mint'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Helios' grown in a container.

Figure 2:
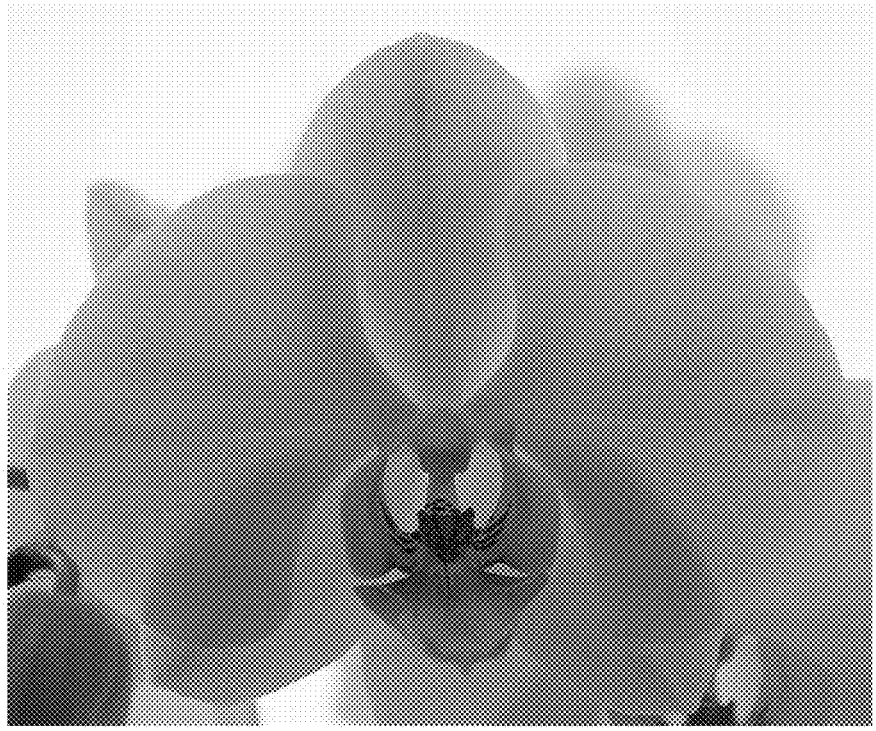

The photograph on the second sheet (FIG. 2) is a close-up view of a typical flower of 'Helios'.

DETAILED BOTANICAL DESCRIPTION

The aforementioned photographs and following observations and measurements describe plants grown during the winter in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27°° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis* hybrida 'Helios'.

Parentage: Female, or seed, parent: Proprietary breeding selection of *Phalaenopsis* hybrida identified as code name C.L., not patented. Male, or pollen, parent: *Phalaenopsis* hybrida 'Emeraude', not patented.

Propagation:

*Type.*—By *in vitro* meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous to vigorous growth habit and moderate to rapid growth rate.

*Plant height, substrate level to top of foliar plane.*—About 20.9 cm.

*Plant height, substrate level to top of floral plane.*—About 62.3 cm.

*Plant diameter or spread.*—About 25 cm.

Leaf description:

*Arrangement and quantity.*—Distichous, simple; sessile; about six to eight fully-developed leaves per plant.

*Length.*—About 17.1 cm.

*Width.*—About 7.3 cm.

*Aspect.*—Semi-erect to horizontal.

*Shape.*—Oblanceolate; slightly carinate.

*Apex.*—Unequal obtuse.

*Base.*—Sheathed. Sheath length: About 1.9 cm. Sheath width: About 1.4 cm. Sheath color, upper and lower surfaces: Close to 143C.

*Margin.*—Entire.

*Texture and luster, upper and lower surfaces.*—Smooth, glabrous; slightly glossy.

*Venation pattern.*—Camptodromous.

*Color.*—Developing leaves, upper surface: Close to a blend of NN137A and 147A; towards the margins and apex, close to NN137C. Developing leaves, lower surface: Close to a blend of 146A and 147A; narrow marginal edges, close to 147A. Fully expanded leaves, upper surface: Close to a blend of 137A and 137B; towards the margins and apex, close to 137D; venation, close to 139A. Fully expanded leaves, lower surface: Close to 146B; narrow marginal edges, close to 147B; venation, close to 137B.

Inflorescence description:

*Appearance and flowering habit.*—Showy zygomorphic flowers arranged on axillary simple or branched racemes; typically two inflorescences develop per plant; each inflorescence with about ten flowers; flowers face mostly outwardly on outwardly arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity and postproduction longevity.*—Long flowering period and good postproduction longevity, individual flowers maintain good substance for about seven weeks on the plant; flowers not persistent.

*Inflorescence length* (*lowermost flower to inflorescence apex*).—About 23.8 cm.

*Inflorescence width.*—About 18.9 cm.

*Flower buds* (*about one week before flower opening*).—Height: About 2 cm. Diameter: About 1.5 cm. Shape: Broadly ovoid. Color: Close to a blend of 145A and 145B.

*Flower size.*—About 9.1 cm (vertical) by 10 cm (horizontal).

*Flower depth.*—About 3.3 cm.

*Petals, quantity and arrangement.*—Three, two lateral petals and one center petal transformed into a labellum.

*Lateral petals.*—Length: About 4.9 cm. Width: About 6.3 cm. Shape: Broadly lunate to close to reniform; not imbricate. Apex: Obtuse. Margin: Entire; not undulate. Texture and luster, upper and lower surfaces: Smooth, glabrous; moderately velvety; matte. Color: When opening, upper surface: Close to a blend of 150D and 157B. When opening, lower surface: Close to 145C; towards the margins and apex, close to 150D. Fully opened, upper surface: Close to 157C; color does not change with subsequent development. Fully opened, lower surface: Close to a blend of 150D and 157B; towards the margins and apex, close to 157B; color does not change with subsequent development.

*Labella.*—Appearance: Three-parted with two lateral lobes and a central lobe. Length, lateral lobes: About 2.4 cm. Width, lateral lobes: About 1.9 cm. Length, central lobe: About 2.5 cm. Width, central lobe: About 0.7 cm to 2.6 cm. Length, cirrhose apices: About 2.8 cm. Shape, lateral lobes: Broadly ovate. Shape, central lobe: Deltoid with a short base and a slightly elongated apex. Apex, lateral lobes: Obtuse. Apex, central lobe: Acute with two cirrhose apices curled upwards and backwards. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 7 mm in width and about 6 mm in height. Color, lateral lobes: When opening and fully opened, upper surface: Close to 150C; towards the apex, close to a blend of 145D and 150D; at the base, tinged with close to N170C with axillary stripes, close to 184B and 184C. When opening and fully opened, lower surface: Close to a blend of 145D and 150D; towards the lower margin, close to 150B; narrow marginal edges, close to 182B. Color, central lobe: When opening, upper surface: Close to a blend of 145D and 150D; narrow apical edges, close to 165B; towards the base, tinged with close to N170C; at the base, close to 149C with radial stripes, close to 184B; cirrhose apices, close to 154A. When opening, lower surface: Close to a blend of 145D and 150D; towards the lateral apices, close to 150B; narrow marginal edges, close to 165B; at the base, close to 149C; cirrhose apices, close to 154A. Fully opened, upper surface: Close to a blend of 145D and 150D; narrow apical edges, close to 182B; towards the base, tinged with close to 182D; at the base, close to 149C with radial stripes, close to 184B; cirrhose apices, close to 154A. Fully opened, lower surface: Close to a blend of 145D and 150D; towards the lateral apices, close to 150B; narrow marginal edges, close to 182D; at the base, close to 149C; cirrhose apices, close to 154A. Color, callosities: When developing: Close to 154C; towards the apex, close to 151C and 151D; fine dots and stripes, close to 176A. Fully developed: Close to 154C; towards the apex, close to 151D; fine dots and stripes, close to 176A.

*Sepals.*—Quantity and arrangement: Three, one upper dorsal sepal and two lower lateral sepals. Length, dorsal sepal: About 5 cm. Width, dorsal sepal: About 3.7 cm. Length, lateral sepals: About 5.1 cm. Width, lateral sepals: About 3.2 cm. Shape, dorsal sepal: Broadly elliptic; flat to slightly concave. Shape, lateral sepals: Ovate; flat to slightly concave. Apex, dorsal sepal: Broadly obtuse. Apex, lateral sepals: Broadly and bluntly acute. Base, dorsal and lateral sepals: Truncate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to a blend of 145D and 150D. When opening, lower surface: Close to 150C; towards the margins and apex, close to 150D. Fully opened, upper surface: Close to 157B; towards the margins and apex, close to a blend of 157B and 157C. Fully opened, lower surface: Close to 145D; towards the margins and apex, close to a blend of 145D and 150D; at the apex, slightly tinged with close to 182D. Color, lateral sepals: When opening, upper surface: Close to a blend of 145D and 150D; towards the base, close to a blend of 145C and 150C. When opening, lower surface: Close to a blend of 145C and 150C. Fully opened, upper surface: Close to 157B; towards the base, close to a blend of 145D and 150D. Fully opened, lower surface: Close to a blend of 145C and 145D; towards the margins and apex, close to a blend of 145D and 150D; at the apex, midvein, slightly tinged with close to 182D.

*Peduncles.*—Length: About 63.1 cm. Diameter: About 6 mm. Strength: Strong. Aspect: Upright to outwardly arching. Texture and luster: Smooth, glabrous; matte. Color: Close to 147A; sparsely covered with fine dots, close to 138B.

*Pedicels.*—Length: About 4.6 cm. Diameter: About 3.25 mm. Strength: Moderately strong. Aspect: About 70° from peduncle axis. Texture and luster: Smooth, glabrous; matte. Color: Close to 145A; proximal end, close to 148A.

*Reproductive organs.*—Androecium: Column length: About 9 mm. Column width: About 6 mm. Column color: Close to 145D. Pollinia quantity: Two. Pollinia diameter (per two pollinia): About 2.25 mm. Pollinia color: Close to 23A. Gynoecium: Stigma length: About 3 mm. Stigma width: About 4 mm. Stigma shape: Reniform. Stigma color: Close to 145D. Ovary length: About 9 mm. Ovary diameter: About 1 mm. Ovary color: Close to 145C.

Seeds and fruits: To date, seed and fruit development have not been observed on plants of the new *Phalaenopsis*.

PATHOGEN & PEST RESISTANCE:

To date, plants of the new *Phalaenopsis* have not been shown to be resistant to pathogens and pests common to *Phalaenopsis* plants.

TEMPERATURE TOLERANCE:

Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Helios' as herein illustrated and described.

* * * * *